(12) United States Patent
Pineau et al.

(10) Patent No.: US 9,351,762 B2
(45) Date of Patent: May 31, 2016

(54) MULTIFUNCTIONAL DEVICE FOR EXPLORATION AND/OR INTERVENTION, ESPECIALLY FOR MEDICAL USE

(76) Inventors: Charles-Henri Pineau, Montauban (FR); Hervé Coupellier, Fabas (FR)

( * ) Notice: Subject to any disclaimer, the term of this patent is extended or adjusted under 35 U.S.C. 154(b) by 1284 days.

(21) Appl. No.: 13/203,163

(22) PCT Filed: Feb. 24, 2010

(86) PCT No.: PCT/FR2010/000173
§ 371 (c)(1),
(2), (4) Date: Aug. 24, 2011

(87) PCT Pub. No.: WO2010/097526
PCT Pub. Date: Sep. 2, 2010

(65) Prior Publication Data
US 2011/0306953 A1  Dec. 15, 2011

(30) Foreign Application Priority Data
Feb. 25, 2009  (FR) ...................................... 09 00853

(51) Int. Cl.
| A61B 17/00 | (2006.01) |
| A61B 17/34 | (2006.01) |
| A61B 17/3205 | (2006.01) |
| A61M 25/01 | (2006.01) |
| A61M 25/00 | (2006.01) |

(52) U.S. Cl.
CPC ....... *A61B 17/3478* (2013.01); *A61B 17/32056* (2013.01); *A61M 25/01* (2013.01); *A61B 2017/00269* (2013.01); *A61B 2017/00353* (2013.01); *A61M 25/0097* (2013.01)

(58) Field of Classification Search
USPC ........................................ 606/1, 130; 600/130
See application file for complete search history.

(56) References Cited

U.S. PATENT DOCUMENTS

| 5,323,768 A | 6/1994 | Saito et al. |
| 5,741,271 A | 4/1998 | Nakao et al. |
| 6,589,231 B1 | 7/2003 | Gobron et al. |
| 2005/0085692 A1 | 4/2005 | Kiehn et al. |
| 2009/0281377 A1* | 11/2009 | Newell et al. ................. 600/104 |
| 2009/0281556 A1* | 11/2009 | Newell et al. ................. 606/144 |
| 2010/0099946 A1* | 4/2010 | Jenkins et al. ................ 600/104 |
| 2011/0282285 A1* | 11/2011 | Blanchard et al. ....... 604/164.08 |

FOREIGN PATENT DOCUMENTS

| EP | 1 002 499 A2 | 5/2000 |
| EP | 1 665 993 A1 | 6/2006 |

* cited by examiner

*Primary Examiner* — William Thomson
*Assistant Examiner* — Jeffrey Lipitz
(74) *Attorney, Agent, or Firm* — Birch, Stewart, Kolasch & Birch, LLP (57) ABSTRACT

The invention relates to a multifunctional device for exploration and/or intervention, especially for medical use, comprising a hollow handle, which is continued by a main catheter, and a carriage which is mounted so as to slide along the handle and which is coupled to an instrument by a mechanical connection extending inside the main catheter. According to the invention, at least one intermediate carriage is mounted so as to slide along the handle, each of said intermediate carriages having an attachment housed in the handle via a longitudinal slot, in the continuation of which there is a secondary catheter extending inside the main catheter. Moreover, an auxiliary carriage is mounted so as to slide along each intermediate carriage, each of said auxiliary carriages being coupled to an instrument by a mechanical connection extending inside the secondary catheter.

20 Claims, 6 Drawing Sheets

Fig 1

MULTIFUNCTIONAL DEVICE FOR EXPLORATION AND/OR INTERVENTION, ESPECIALLY FOR MEDICAL USE

The invention relates to a multifunctional device for exploration and/or intervention, especially for medical use.

During medical examinations such as endoscopies, for example, it is common for the specialist to be called upon to perform a delicate operation requiring several instruments.

At the present time, one way of achieving this involves the use of an instrument known as a dual-channel therapeutic endoscope. However, such endoscopes are costly and few institutions are in a position to make them available to practitioners.

Thus, the technique most commonly adopted consists of successively using different instruments such as described in particular in patent application EP 1 665 993, including a hollow handle continued by a flexible conduit, known as the main catheter, and a carriage mounted so as to slide longitudinally along the handle, connected to an instrument by a mechanical connection extending inside the main catheter so as to enable the actuation and/or movement of the said instrument during longitudinal movements of the said carriage.

Thus, for example, the mucosectomy procedure involves three successive steps each requiring a separate apparatus: staining, separation, resection. However, this technique entails on one hand an additional financial cost and, secondly and more importantly, results in a loss of time which can be prejudicial by the fact that it occurs at a highly delicate moment.

The present invention aims to overcome this drawback and has the principal object of providing a multifunctional device integrating several instruments capable of being positioned together at an intervention site and capable of being operated individually or simultaneously, optionally by the same operator.

A further object of the invention is to provide a multifunctional device whose space requirement is comparable to that of a conventional instrument.

To this end, the invention discloses a multifunctional device for exploration and/or intervention, especially for medical use, including:
  a hollow handle continued by a flexible conduit, known as the main catheter,
  a carriage, known as the end carriage, mounted so as to slide longitudinally along an end portion of the handle located opposite the main catheter, connected to an instrument by a mechanical connection extending inside the said main catheter to allow the said instrument to be actuated and/or moved during longitudinal movements of the said end carriage.

According to the invention, the multifunctional device is characterised in that:
  the handle includes at least one intermediate portion having a peripheral wall in which is formed a longitudinal slot,
  a carriage, known as the intermediate carriage, is mounted so as to slide longitudinally along each intermediate portion of the handle,
  each of the said intermediate carriages including an attachment:
  suitably shaped to fit into the handle through the longitudinal slot formed in the corresponding intermediate portion,
  pierced with a longitudinal slot in the continuation of which is secured a flexible conduit, known as the secondary catheter, extending into the main catheter,
  and defining a conduit for passage of the mechanical connection linking the end carriage and its associated instrument, and optionally of each secondary catheter associated with an intermediate carriage mounted on an intermediate portion located between the end portion and the intermediate portion concerned,
  an auxiliary carriage is mounted so as to slide longitudinally along each intermediate carriage, each of the said auxiliary carriages being connected to an instrument by a mechanical connection extending into the slot formed in the attachment of the said intermediate carriage and in the secondary catheter associated with this intermediate carriage, so as to enable the said instrument to be actuated and/or moved during longitudinal movements of the said auxiliary carriage.

(It will be noted that, according to the invention, the term handle is understood to define a rigid body that can be manipulated by hand and having one or more rigid adapters or connectors for connecting a main catheter comprising a flexible tube to the said handle.)

According to the invention, at least two instruments, respectively connected to the end carriage and to each auxiliary carriage, can be positioned in the immediate vicinity of an intervention site, and can be used successively or simultaneously. Also, in an essential manner, all of the carriages including the intermediate and end carriages, and therefore the associated catheters including the secondary and main catheters, can be moved independently of each other, offering the possibility of relative movement of the instruments during the intervention, and numerous possibilities for relative positioning of the said instruments.

In addition, the multifunctional device is designed so that each secondary catheter extends inside the main catheter housing the mechanical connection connecting the end carriage to its associated instrument. Thus, the cross-section of the main catheter is comparable to that of the catheter of a known conventional instrument.

According to an advantageous embodiment, the multifunctional device according to the invention additionally includes an adapter for connecting a fluid injection device, formed in an end portion of the handle opposite the end portion whereon is mounted the end carriage, and adapted to emerge into the handle and to communicate with the main catheter.

Thus, not only is the main catheter designed to house the mechanical connection between the end carriage and the associated instrument, as well as each secondary catheter, but it also forms, without increasing its space requirement, a flow channel for a fluid.

Such an arrangement imparts to the device according to the invention an additional function of injecting a fluid, such as a cleaning or staining fluid, into the main catheter.

Furthermore, according to this embodiment, the main catheter advantageously houses a transverse membrane positioned in the vicinity of the free end of the said main catheter, the said membrane being pierced with holes for the passage of each secondary catheter and the mechanical connection connecting the end carriage and its associated instrument, and being pierced with holes designed to allow an injection of fluid in the form of a spray.

In addition, to the same end of enabling an injection of fluid in spray form, the catheter preferably includes an end portion of tapered shape.

According to another advantageous embodiment of the invention, the multifunctional device according to the invention also includes an adapter for introducing a guide wire, formed in an end portion of the handle opposite the end portion whereon is mounted the end carriage, and adapted to allow the introduction of a guide wire into the main catheter.

Thus, not only is the main catheter designed to house the mechanical connection connecting the end carriage to the associated instrument, as well as each secondary catheter, but it also forms, without increasing its space requirement, a conduit for introducing a guide wire.

According to another advantageous characteristic of the invention, each carriage includes a shell having a shape adapted to cover the handle.

In addition, each intermediate carriage and the handle have sections preferably in this case including at least one longitudinal ridge adapted so as to obtain a relative locking in rotation of the said intermediate carriage(s) and the handle.

Furthermore, in order to obtain stable relative positions of each intermediate carriage in relation to the handle, the shell of each intermediate carriage and the handle advantageously include opposing faces having conjugate members for reversibly locking the translational movement of the said elements.

According to another advantageous characteristic of the invention, the shell of each intermediate carriage includes a longitudinal notch defining a runner adapted to accommodate an auxiliary carriage formed by a slide capable of sliding in said runner.

Furthermore, in an advantageous manner according to the invention, at least one carriage of the multifunctional device, an end carriage and/or auxiliary carriage, is connected to its associated instrument by an electrically conductive mechanical connection, and includes a connector for connecting to an electric scalpel, electrically connected to the mechanical connection associated with the said carriage.

Other characteristics, objects and advantages of the invention will become apparent from the following detailed description with reference to the accompanying drawings which show, by way of non-limitative example, a preferred embodiment thereof. In the drawings.

Figure 1:
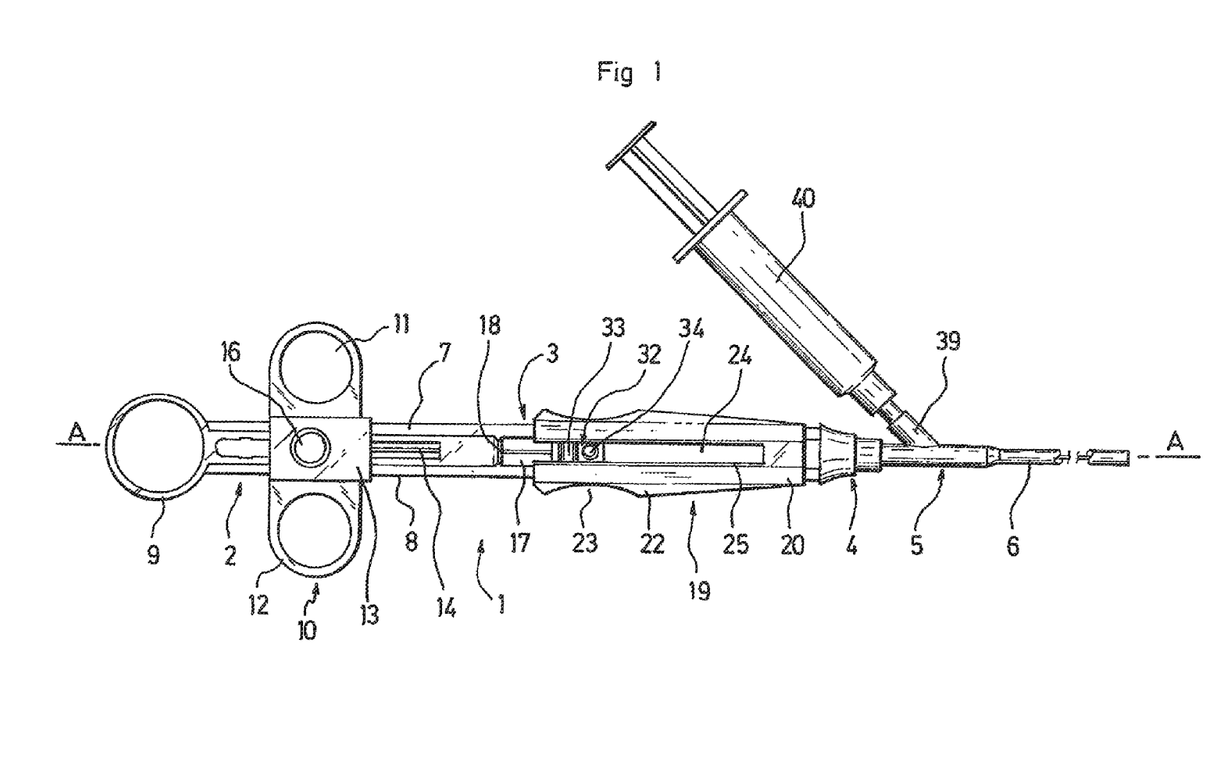
FIG. 1 is a longitudinal top view of a multifunctional device according to the invention.

(For the sake of simplicity and clarity of the description, the multifunctional device according to the invention is described hereinbelow with reference to FIG. 1 attached as a top view of the device, and the terms "upper, lower, side..." in particular are used in accordance with this reference. Also, the terms such as posterior and anterior are used with the assumption that the device is being held in an operator's hand, and the terms posterior and rear typically correspond to the portions of the device closest to the operator's hand).

The multifunctional device for exploration and/or intervention shown by way of example in the Figures is intended especially for medical use.

Furthermore, in the accompanying figures, the multifunctional device is equipped with instruments particularly adapted for the performance of medical examinations such as endoscopies.

The multifunctional device according to the invention includes, in the first place, a rigid handle 1 which is subdivided longitudinally into:
 a posterior end portion 2,
 an intermediate portion 3,
 a reducing adapter 4 of generally conical shape,
 and an anterior tubular conduit 5 at the end of which is connected a flexible tube 6 constituting the main catheter of the multifunctional device.

The posterior section 2 of the handle 1 principally comprises two parallel longitudinal rails 7, 8 extending from a posterior ring 9 providing thumb purchase, along which is mounted slidably over a travel "a" of about eight centimeters a carriage 10, known as the end carriage, comprising:
 a central core 13 adapted to slide along the rails 7, 8,
 and two side wings 11, 12 extending on either side of the central core 13, each consisting of a ring for finger purchase.

This first carriage 10 is connected to an instrument by a mechanical connection extending inside the main catheter 6, and its function is to actuate and/or move the said instrument during longitudinal movements of the said carriage.

Figure 8A:
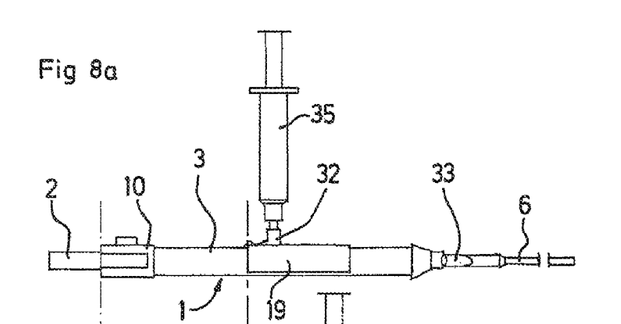
FIGS. 8a to 8d are diagrams showing four distinct operating states of the multifunctional device according to the invention.
Figures 8B, 8C:
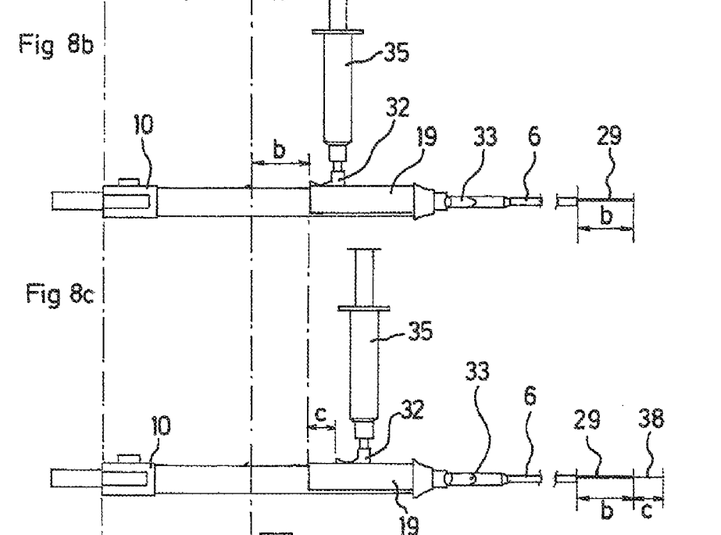
Figure 8D:
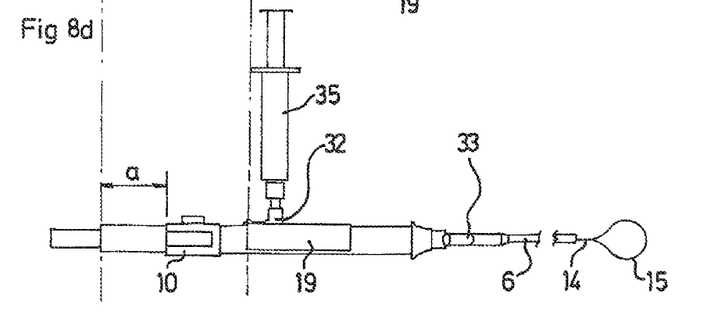

In the example shown in the Figures, the mechanical connection consists of a cable made of an electrically conductive material 14 of which the end forms a ring 15 constituting a instrument known as a "loop" adapted:
 to be housed inside the main catheter 6 in at least a partially closed condition, in the retracted position of the end carriage shown in FIG. 8a,
 to extend in the continuation of the main catheter 6, in a deployed open condition, in the forward position of the end carriage 10 shown in FIG. 8d, where the said end carriage has completed a translational movement of a distance equal to "a" from its retracted position.

In addition, the central core 13 of the end carriage 10 includes a connector 16 for connecting to an electric scalpel, electrically connected to the cable 14 secured to the said carriage, thereby imparting to the loop 15 an additional function of a cutting instrument.

Figure 2:
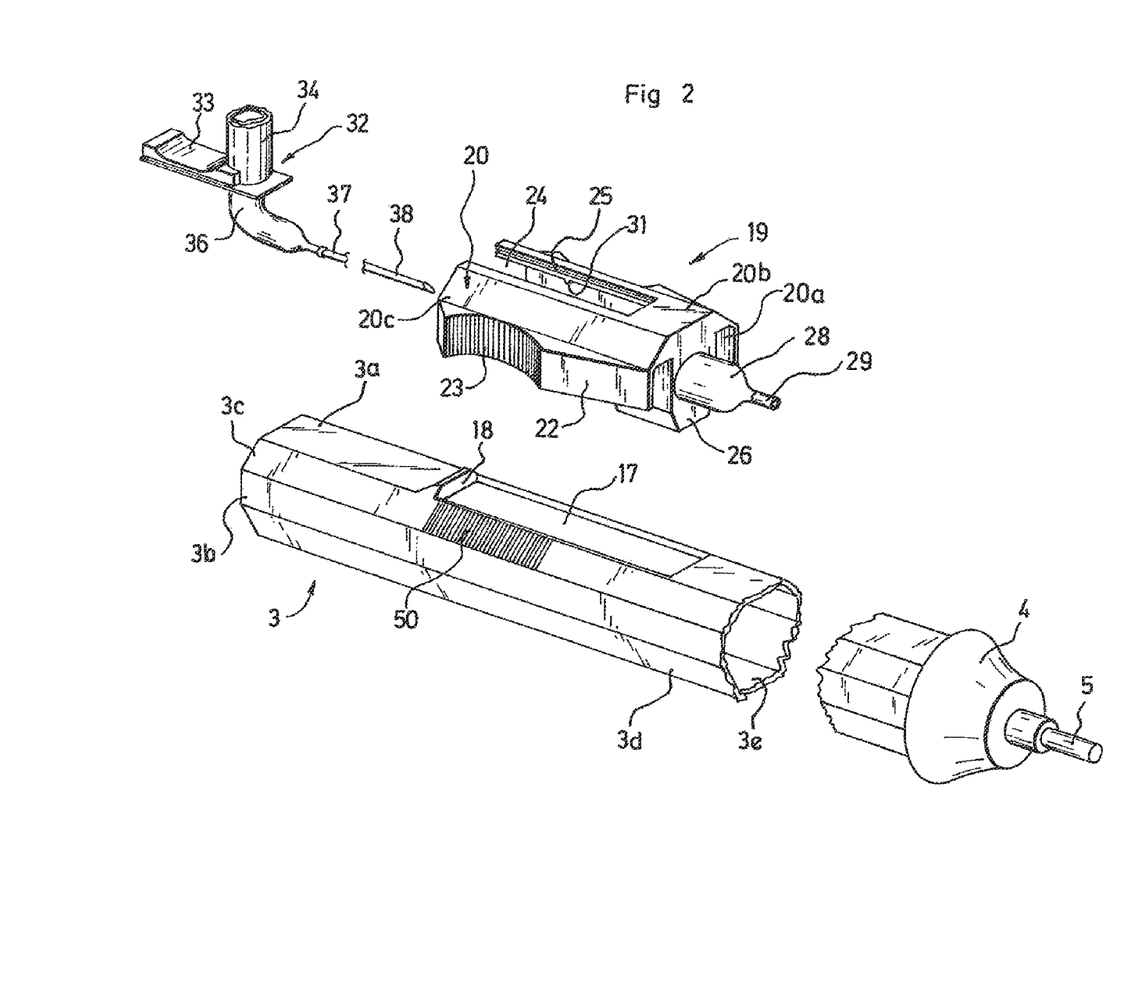
FIG. 2 is an exploded perspective view showing the intermediate portion of a handle, an intermediate carriage and an auxiliary carriage of a multifunctional device according to the invention.

The intermediate portion 3 of the handle 1 is composed of a tubular body of octagonal cross-section including an upper face 3a, two parallel sides faces such as 3b, two oblique upper faces such as 3c, joining the upper face 3a with the side faces 3b, two lower oblique faces 3d and a lower face 3e.

Firstly regarding the intermediate portion 3, the upper face 3a is pierced by a longitudinal slot 17 of rectangular shape, having a length of about eight centimeters. Furthermore, this slot is delimited at its posterior end by a transverse stop fin 18 arranged so as to extend in projection from the upper surface 3a.

The multifunctional device according to the invention includes a carriage 19, known as the intermediate carriage, mounted so as to slide along the intermediate portion 3, and principally comprising:

a shell 20 of generally semi-octagonal shape adapted to cover the upper face 3a, the oblique upper faces 3c and the side faces 3b of the intermediate portion 3, and an attachment 26 positioned at the anterior end of the intermediate carriage 19, and generally shaped as a rectangular parallelepiped adapted to extend inside the intermediate portion 3 of the handle 1 through the slot 17.

Figure 5:
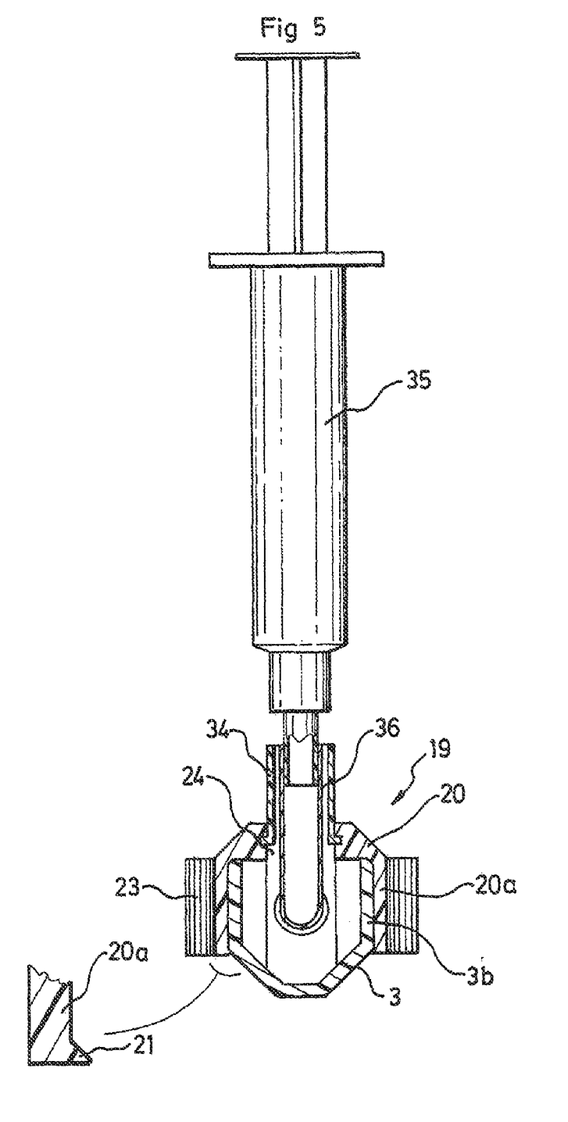
FIG. 5 is a transverse cross-section, in a plane B of FIG. 4, of the multifunctional device according to the invention.

The shell 20 of the intermediate carriage 19 includes, in the first place, two side walls such as 20a disposed so as to overlap onto the side faces 3b of the intermediate portion 3, and each extended by a longitudinal oblique rim 21, shown in FIG. 5, adapted to form a resilient hook for snapping the intermediate carriage 19 onto the intermediate portion 3.

Each of the side walls 20a additionally includes a thickening 22 formed on the outer face of the shell 20, and in which is formed a posterior longitudinal indentation 23 having a grooved surface, providing finger purchase for the intermediate carriage 19.

The shell 20 of the intermediate carriage 19 additionally includes an upper face 20b in which is formed a notch 24 extending from the posterior end of the said upper surface, of which the longitudinal inner edges 25 are shaped so as to define a runner adapted to accommodate an auxiliary carriage 32 consisting of a slide.

The shell 20 also includes two oblique upper faces 20c on the underside of each of which is formed a transverse bead 31 for reversible locking adapted to cooperate with transverse grooves 50 formed on the oblique upper faces 3c of the intermediate portion 3, so as to obtain stable relative positions of the intermediate carriage 19 along the handle 1.

The attachment 26 of the intermediate carriage 19 is, in the first place, pierced by a longitudinal slot 27 and includes, in the continuation of the said slot, an adapter 28 for connecting a flexible tube 29 forming a catheter known as the secondary catheter adapted to extend inside the main catheter 6. Furthermore, the attachment 26 is also pierced by a conduit 30 for passage of the cable 14 connecting the end carriage 10 and its associated instrument (loop) 15.

The respective dimensions of the slot 17 and the attachment 26 of the intermediate carriage 19 are adapted to allow a longitudinal movement of the said carriage over a travel distance "b" of about four centimeters, between:

a retracted position of the intermediate carriage 19, shown in FIG. 8a, in which the said intermediate carriage is abutted against the stop fin 18, and the secondary catheter 29 is retracted inside the main catheter 6, and an extended position of the intermediate carriage 19, shown in FIG. 8b, in which an end portion of a length substantially equal to "b" of the secondary catheter 29 extends inside the continuation of the end of the main catheter 6.

In addition, over this travel distance, stable intermediate positions 10 are defined by the cooperation of the locking beads 31 with the grooves 50.

It will be noted that the end carriage 10 of the multifunctional device according to the invention can also be composed of a carriage of the same design as the intermediate carriage described hereinabove.

As indicated above, the multifunctional device according to the invention also includes a third carriage 32, known as the auxiliary carriage, comprising a slide adapted to move longitudinally relative to the intermediate carriage 19.

The slide 32 has an upper face on which is formed a posterior longitudinal indentation 33 having a grooved surface for operating the said slide using the fingers.

Figure 4:
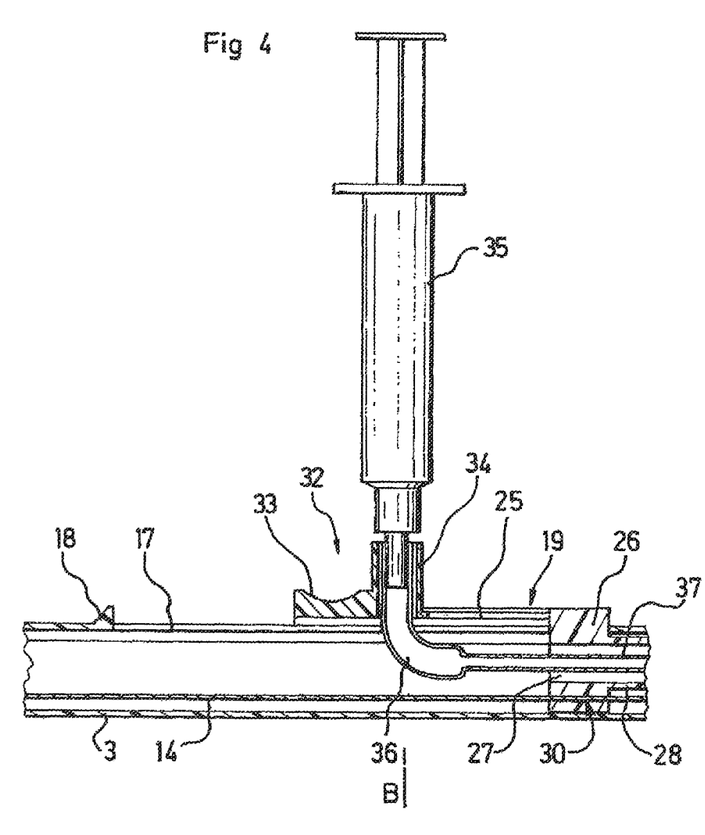
FIG. 4 is a partial longitudinal section in an axial plane A of a multifunctional device according to the invention in which the auxiliary carriage is equipped with a syringe shown not in cross-section.

In addition, the slide 32 includes an adapter 34 for connecting a syringe 35 communicating, via an elbow piece 36, with a flexible conduit 37 adapted to extend inside the slot 27 formed in the attachment 26 of the intermediate carriage 19 then inside the secondary catheter 29, and on the end of which is mounted an injection needle 38.

The respective dimensions of the notch 24 and the slide 32 are adapted to allow a longitudinal movement of the auxiliary carriage over a useful travel distance "c" of about 1.5 centimeters, between:

a forward position of the auxiliary carriage 32, shown in FIG. 8c, in which an injection portion of a length substantially equal to "c" of the needle 38 extends inside the continuation of the end of the secondary catheter 29, and retracted positions of the auxiliary carriage 32, such as that shown in FIG. 8b, in which the needle 38 is retracted inside the secondary catheter 29. It will be noted that the extreme retracted position of the auxiliary carriage 32 corresponds to a stop position of the said auxiliary carriage against the stop ridge 18.

In addition, depending on the requirements related to the associated instruments, the movement of the auxiliary carriage may consist either of a unidirectional movement or a bidirectional movement on either side of a median neutral position.

The multifunctional device according to the invention additionally includes an adapter 39 for connecting a syringe 40 disposed in an intermediate position of the anterior tubular conduit 5, so as to be in direct communication with the main catheter 6. As shown in FIG. 1, this adapter 39 extends in a plane orthogonal to the plane in which the adapter 34 extends, along an axis inclined at 45° backwards relative to the longitudinal axis of the handle 1.

Such an arrangement enables a fluid to be injected into the main catheter 6, such as for example a cleaning fluid, a staining fluid, etc.

Figures 3A, 3B, 6, 7:
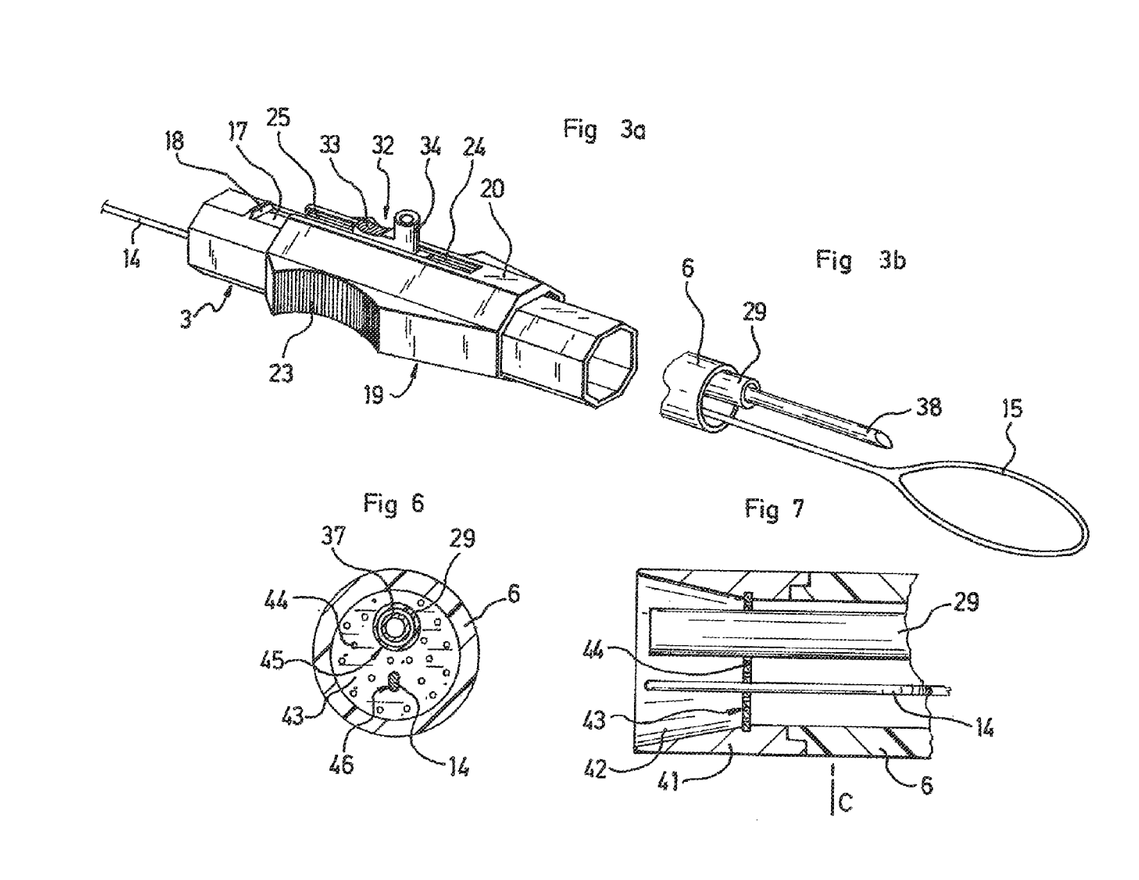
FIG. 3a is a partial perspective view showing, in assembled form, the intermediate portion of a handle, an intermediate carriage and auxiliary carriage of a multifunctional device according to the invention.
FIG. 3b is a perspective view showing, at an enlarged scale, the end of a main catheter and a secondary catheter together with associated instruments, of a multifunctional device according to the invention.
FIG. 6 is a transverse cross-section, at an enlarged scale, in a plane C of FIG. 7, of the end portion of the main catheter of a multifunctional device according to the invention.
FIG. 7 is a longitudinal section, at an enlarged scale, of the end portion of the main catheter of the multifunctional device.

In addition, the main catheter 6 then includes, as shown in FIGS. 6 and 7, an anterior adapter 41 designed to be mounted, for example by interlocking, onto the free end of the said main catheter, the said adapter:

including an end portion 42 of internally tapering shape, housing a transverse membrane 43 pierced, on one hand, with holes 45, 46 for the passage of each secondary catheter 29 and of the cable 14 connecting the end carriage 10 and its associated instrument 15 and, on the other hand, injection apertures 44 designed to permit an injection of fluid in the form of a spray.

It will be noted that the adapter 39 can be used for different purposes and in particular can consist of an adapter for introducing a guide wire designed to enable a guide wire to be inserted into the main catheter 6.

In this case, additionally, the main catheter 6 is not provided with the anterior adapter 41 and the membrane 43.

The multifunctional device described hereinabove, equipped with a diathermy loop 15 connected to an electric scalpel, a sclerosis needle 38 and a channel for injecting a staining fluid, is particularly intended for medical use, for example to perform a mucosectomy, Specifically, the device can be used to perform the three successive steps of a mucosectomy, namely: vital staining, submucosal injection and resection of the polyp.

Firstly, vital staining is performed using a syringe 40 connected to the adapter 39 making it possible to deliver the stainer directly into the main catheter 6, then to distribute the stainer in the form of a spray by virtue of the membrane 43.

At the submucosal injection stage, the latter is greatly facilitated by the presence at the injection site of the main catheter 6 and optionally the loop 15 which make it possible to obtain better exposure of the lesion and a submucosal injection of good quality.

Similarly, the third stage of polyp resection, carried out using the loop 15, is greatly facilitated by the presence of the secondary catheter 29 and optionally of the needle 38, which makes it possible to obtain better exposure of the lesion to be treated.

Additionally, all of these operations can be performed by a single operator.

Many other applications, especially in the medical field, are possible using multifunctional devices according to the invention equipped with various specific instruments.

Thus, by way of examples, mention may be made of the following applications in gastrointestinal endoscopy:
lavage/stain-loop-clamp
lavage/stain-loop-"endoloop"
lavage/stain-loop-hemostatic clip,
lavage/stain-submucosal dissection knife ("flush knife")-clamp.

By way of further application, mention may also be made of: sphincterotomy/infundibulotomy/guidewire, etc.

The invention claimed is:

1. A multifunctional device for exploration and/or intervention, for medical use, comprising:
a hollow handle extended by a main catheter,
an end carriage, mounted so as to slide longitudinally along an end portion of the handle located opposite the main catheter, connected to a first instrument by a mechanical connection extending inside the said main catheter to allow the said first instrument to be actuated and/or moved during longitudinal movements of the said end carriage,
the said multifunctional device being such that:
the handle includes one intermediate portion having a peripheral wall in which is formed a longitudinal slot,
an intermediate carriage, is mounted so as to slide longitudinally along the intermediate portion of the handle, said intermediate carriage including an attachment:
suitably shaped to fit into the handle through the longitudinal slot formed in the intermediate portion,
pierced with a longitudinal slot in the continuation of which is secured a secondary catheter, extending into the main catheter,
and defining a conduit for passage of the mechanical connection linking the end carriage and the first instrument,
an auxiliary carriage is mounted so as to slide longitudinally along the intermediate carriage, said auxiliary carriage being connected to a second instrument by a mechanical connection extending into the slot formed in the attachment of the said intermediate carriage and in the secondary catheter associated with this intermediate carriage, so as to enable the said second instrument to be actuated and/or moved during longitudinal movements of the said auxiliary carriage.

2. The multifunctional device according to claim 1, further comprising:
an adapter for connecting a fluid injection device, formed in an end portion of the handle opposite the end portion whereon is mounted the end carriage, and adapted to emerge into the handle and to communicate with the main catheter.

3. The multifunctional device according to claim 2, wherein the main catheter houses a transverse membrane positioned at the free end of the said main catheter, the said membrane being pierced with holes for the passage of the secondary catheter and the mechanical connection connecting the end carriage and the first instrument, and being pierced with injection holes designed to allow an injection of fluid in the form of a spray.

4. The multifunctional device according to claim 3, wherein the main catheter includes an end portion of tapered shape.

5. The multifunctional device according to claim 3, wherein the intermediate carriage includes a shell suitably shaped to cover the handle.

6. The multifunctional device according to claim 2, wherein the main catheter includes an end portion of tapered shape.

7. The multifunctional device according to claim 6, wherein the intermediate carriage includes a shell suitably shaped to cover the handle.

8. The multifunctional device according to claim 2, further comprising:
an adapter for introducing a guide wire, formed in an end portion of the handle opposite the end portion whereon is mounted the end carriage, and adapted to allow the introduction of a guide wire into the main catheter.

9. The multifunctional device according to claim 2, wherein the intermediate carriage includes a shell suitably shaped to cover the handle.

10. The multifunctional device according to claim 2, wherein at least one carriage, an end carriage and/or auxiliary carriage, is connected to its associated, first or second, instrument by an electrically conductive mechanical connection, and includes a connector electrically connected to the mechanical connection associated with the said carriage.

11. The multifunctional device according to claim 1, further comprising:
an adapter for introducing a guide wire, foamed in an end portion of the handle opposite the end portion whereon is mounted the end carriage, and adapted to allow the introduction of a guide wire into the main catheter.

12. The multifunctional device according to claim 11, wherein the intermediate carriage includes a shell suitably shaped to cover the handle.

13. The multifunctional device according to claim 1, wherein the intermediate carriage includes a shell suitably shaped to cover the handle.

14. The multifunctional device according to claim 13, wherein the intermediate carriage and the handle have sections including at least one longitudinal ridge adapted so as to obtain a relative locking in rotation of the said intermediate carriage and the handle.

15. The multifunctional device according to claim 14, wherein the shell of the intermediate carriage and the handle include opposing faces having conjugate members for reversibly locking the translational movement of the said elements.

16. The multifunctional device according to claim 14, wherein the shell of the intermediate carriage includes a longitudinal notch defining a runner adapted to accommodate an auxiliary carriage formed by a slide capable of sliding in said runner.

17. The multifunctional device according to claim 13, wherein the shell of the intermediate carriage and the handle include opposing faces having conjugate members for reversibly locking the translational movement of the said elements.

18. The multifunctional device according to claim 17, wherein the shell of the intermediate carriage includes a longitudinal notch defining a runner adapted to accommodate an auxiliary carriage formed by a slide capable of sliding in said runner.

19. The multifunctional device according to claim 13, wherein the shell of the intermediate carriage includes a longitudinal notch defining a runner adapted to accommodate an auxiliary carriage formed by a slide capable of sliding in said runner.

20. The multifunctional device according to claim 1, wherein at least one carriage, an end carriage and/or auxiliary carriage, is connected to its associated, first or second, instrument by an electrically conductive mechanical connection, and includes a connector electrically connected to the mechanical connection associated with the said carriage.

* * * * *